US012607698B2

(12) United States Patent
Lane et al.

(10) Patent No.: US 12,607,698 B2
(45) Date of Patent: Apr. 21, 2026

(54) WIRELESS GATING SYSTEM FOR MAGNETIC RESONANCE IMAGING

(71) Applicant: Ivy Biomedical Systems, Inc., Branford, CT (US)

(72) Inventors: Joseph Lane, Branford, CT (US); Ryan Mcguire, Orange, CT (US)

(73) Assignee: Ivy Biomedical Systems, Inc., Branford, CT (US)

( * ) Notice: Subject to any disclaimer, the term of this patent is extended or adjusted under 35 U.S.C. 154(b) by 1010 days.

(21) Appl. No.: 17/746,041

(22) Filed: May 17, 2022

(65) Prior Publication Data
US 2023/0393225 A1     Dec. 7, 2023

(51) Int. Cl.
*A61B 5/00*      (2006.01)
*A61B 5/055*     (2006.01)
*G01R 33/567*    (2006.01)

(52) U.S. Cl.
CPC .......... *G01R 33/5673* (2013.01); *A61B 5/055* (2013.01); *A61B 5/7292* (2013.01)

(58) Field of Classification Search
CPC .... G01R 33/5673; A61B 5/055; A61B 5/7292
See application file for complete search history.

(56) References Cited

U.S. PATENT DOCUMENTS 7,595,697 B2     9/2009  Tuccillo
2016/0274203 A1*  9/2016  James ................ G01R 33/4835

FOREIGN PATENT DOCUMENTS

KR     1020080025456 A      3/2008

OTHER PUBLICATIONS

Verma, R. et al., "An Integration of Improved Median and Morphological Filtering Techniques for Electrocardiogram Signal Processing", in the IEEE International Advance Computing Conference, pp. 1223-1228, 2013.
Schmidt, M et al., " Filtering of ECG signals distorted by magnetic field gradients during MRI using non-linear filters and higher-order statistics", in De Gruyter. pp. 395-406, 2018.
English-Language, machine translation of Korean publication No. KR 10-20080025456, published Mar. 21, 2008; Google Patents; 18 pages.

* cited by examiner

*Primary Examiner* — Joel F Brutus
(74) *Attorney, Agent, or Firm* — Sterne, Kessler, Goldstein & Fox P.L.L.C.

(57)            ABSTRACT

An example magnetic resonance imaging (MRI) system uses magnetic fields and radio frequency waves to generate anatomical images of a biological organism, such as a human body, for example. The example MRI system can implement a prospective gating technique, such as cardiac gating and/or respiratory gating, to provide some examples, to improve the image quality of the anatomical images. The prospective gating technique utilizes one or more physiological events of the biological organism to trigger the example MRI system to image the biological organism at specific times to improve the image quality of the anatomical images, compensating example for interference that may be introduced by the magnetic fields and/or the radio frequency waves.

18 Claims, 6 Drawing Sheets

WIRELESS GATING SYSTEM FOR MAGNETIC RESONANCE IMAGING

BACKGROUND

Figure 1:
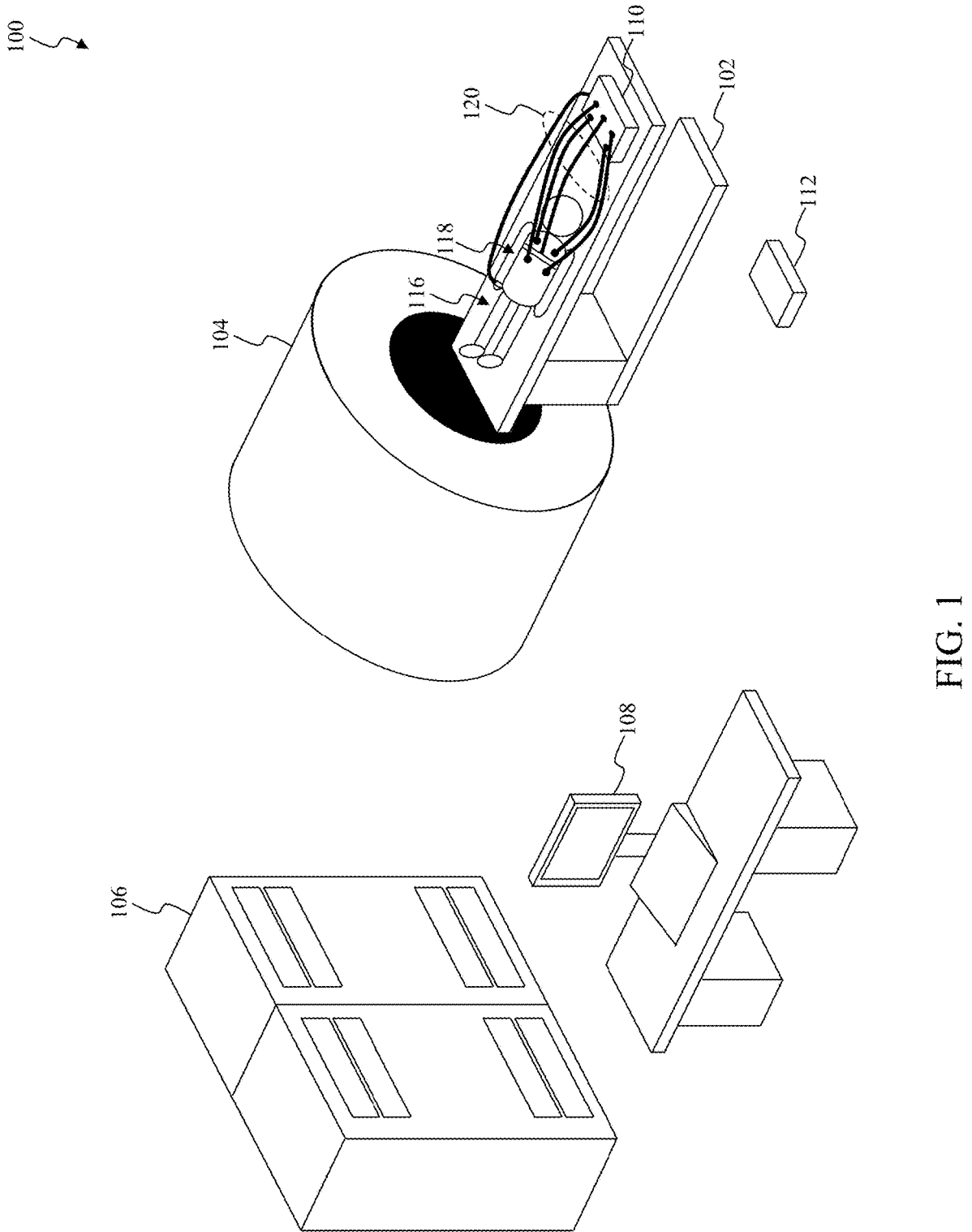

Magnetic resonance imaging (MRI) is a medical imaging technique used in radiology to generate anatomical images of a biological organism. MRI is widely used in hospitals and clinics for medical diagnosis, staging and follow-up of various disease. MRI can be used by medical personnel to examine the brain, spinal cord, bones, joints, the heart, blood vessels, and other internal organs of the biological organism. For example, MRI can be used by medical personnel to evaluate the structure of the heart and aorta to detect aneurysms or tears. As another example, MRI can be used by medical personnel to evaluate glands and organs within the abdomen of the biological organism and can provide accurate information about the structure of the joints, soft tissues, and bones of the biological organism.

BRIEF DESCRIPTION OF THE DRAWINGS/FIGURES

Figure 2:
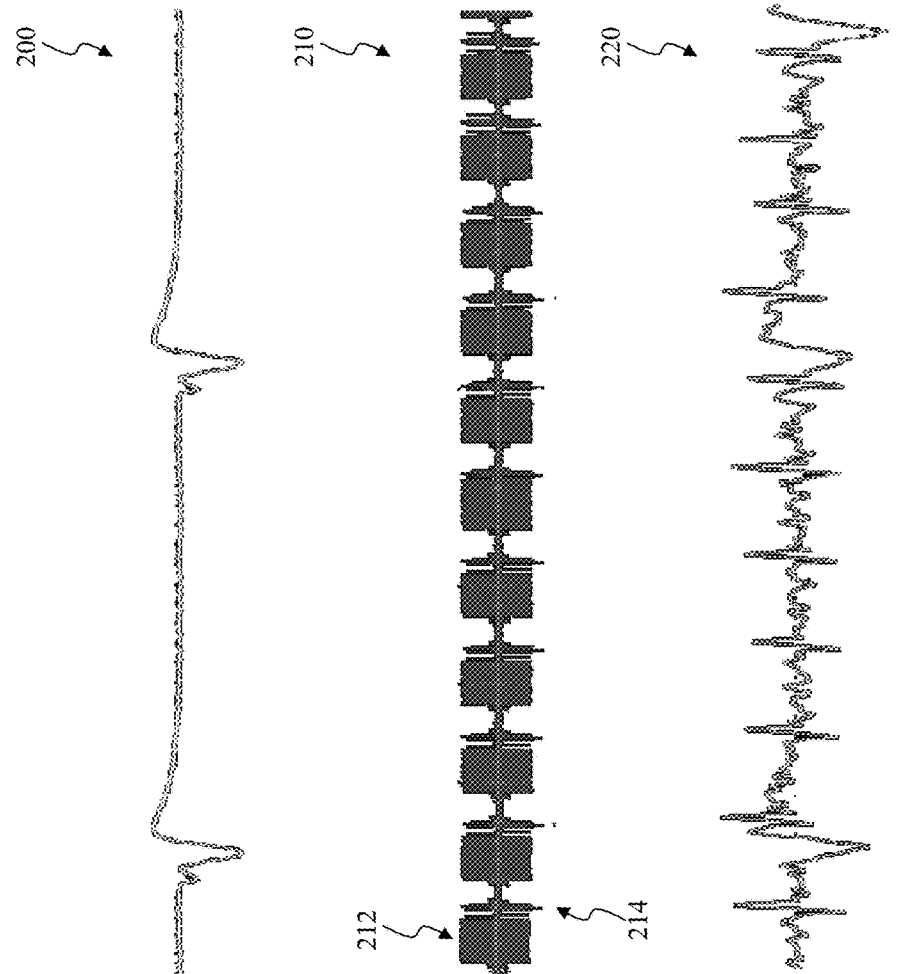
Figure 3:
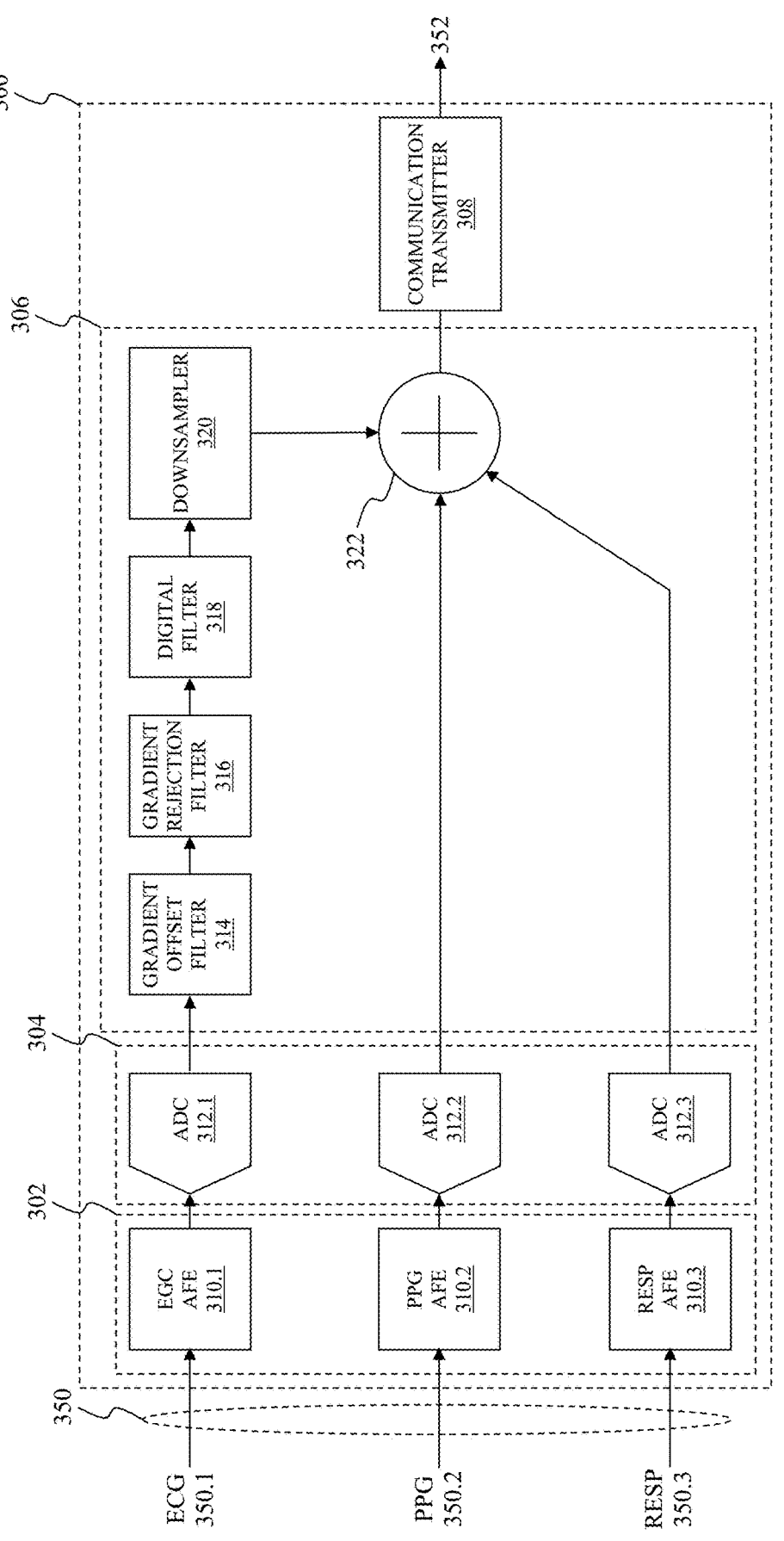
Figure 4:
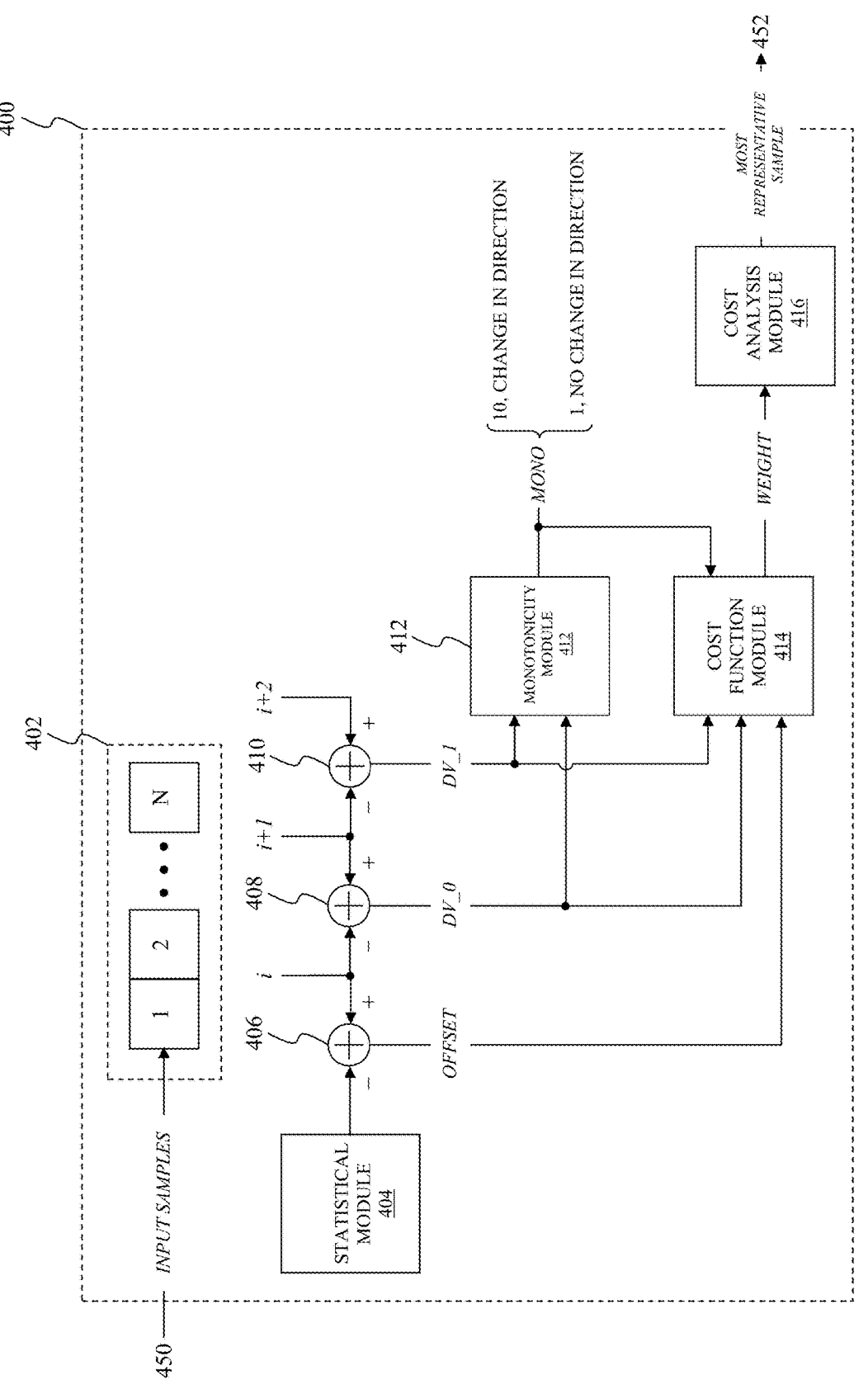
Figure 5:
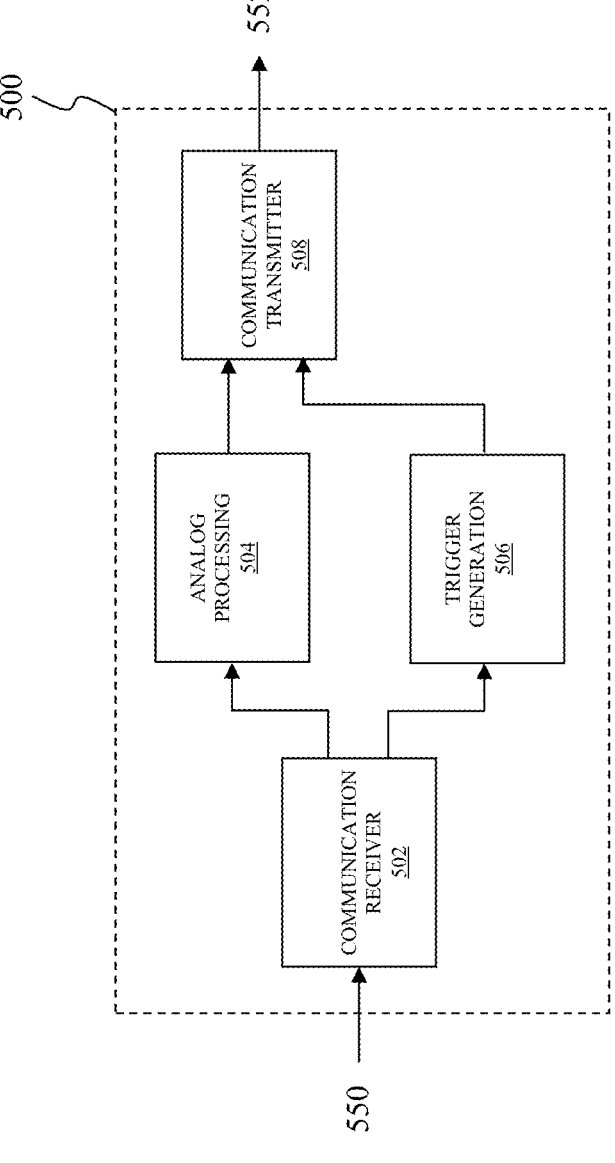
Figure 6:
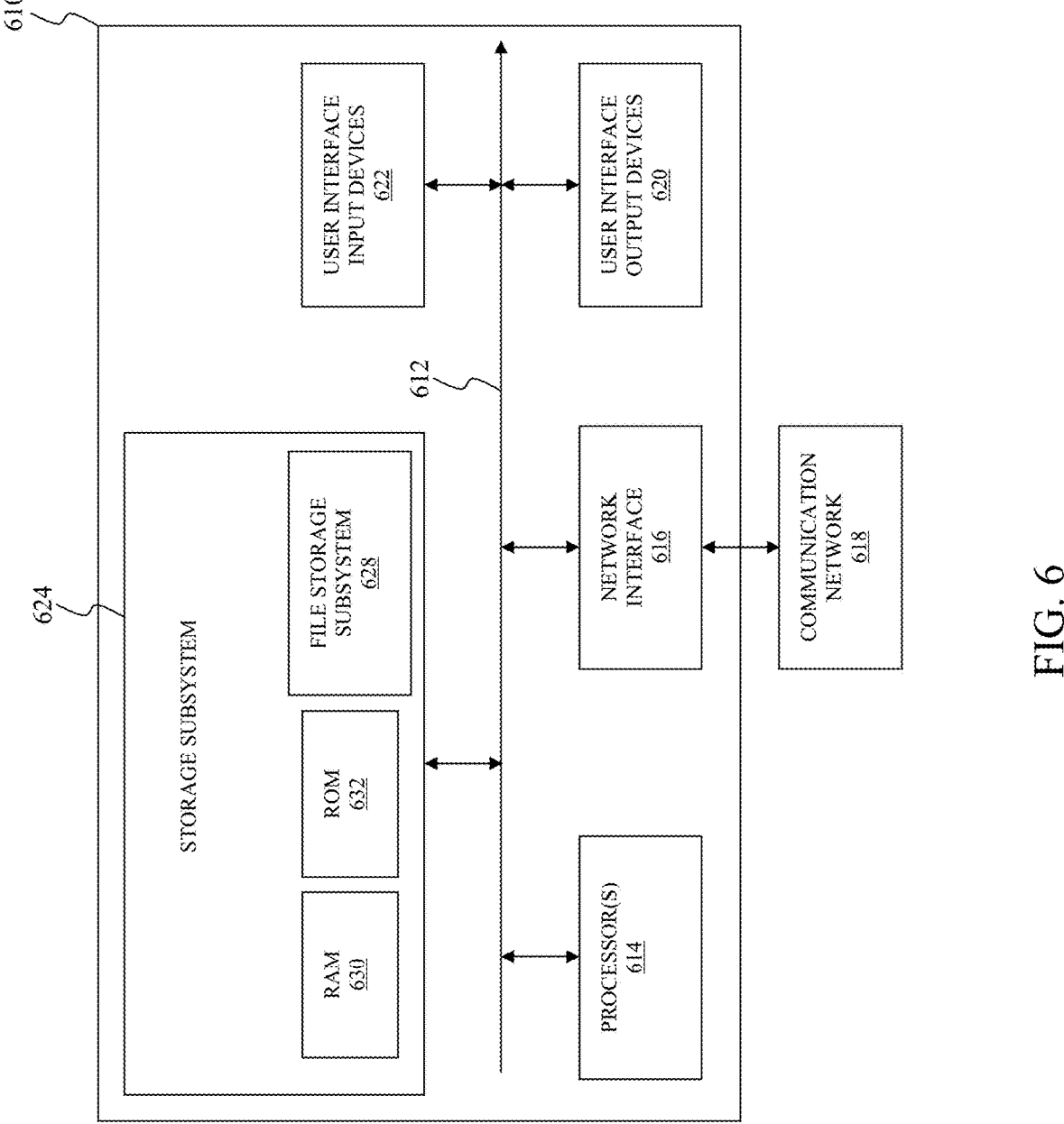

The accompanying drawings, which are incorporated herein and form a part of the specification, illustrate the present disclosure and, together with the description, further serve to explain the principals thereof and to enable a person skilled in the pertinent art to make and use the same. Aspects of the present disclosure are best understood from the following detailed description when read with the accompanying figures. It is noted that, in accordance with the standard practice in the industry, features are not drawn to scale. In fact, the dimensions of the features may be arbitrarily increased or reduced for clarity of discussion. In the drawings:

FIG. 1 graphically illustrates a simplified block diagram of an example magnetic resonance imaging (MRI) system in accordance with some example embodiments of the present disclosure;

FIG. 2 graphically illustrates various signals within the example MRI imaging system in accordance with some example embodiments of the present disclosure;

FIG. 3 graphically illustrates a block diagram for an example gating transmitter that can be implemented within the example MRI imaging system in accordance with some example embodiments of the present disclosure;

FIG. 4 graphically illustrates a block diagram for an example gradient offset filter that can be implemented within the example gating transmitter in accordance with some example embodiments of the present disclosure;

FIG. 5 graphically illustrates a block diagram for an example gating receiver that can be implemented within the example MRI imaging system in accordance with some example embodiments of the present disclosure; and FIG. 6 graphically illustrates a simplified block diagram of a computer system suitable for use with embodiments described herein according to some example embodiments of the present disclosure.

In the accompanying drawings, like reference numbers indicate identical or functionally similar elements. Additionally, the left most digit(s) of a reference number identifies the drawing in which the reference number first appears.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the examples. This repetition does not in itself dictate a relationship between the embodiments and/or configurations discussed.

Overview

An example magnetic resonance imaging (MRI) system uses magnetic fields and radio frequency waves to generate anatomical images of a biological organism, such as a human body, to provide an example. The image quality, for example, the contrast and spatial resolution, of the anatomical images generated by the example MRI system can be less than optimal because of one or more physiological events of the biological organism, for example, the heartbeat and/or the respiration of the biological organism. As to be described in further detail below, the example MRI system can implement a prospective gating technique, such as cardiac gating, and/or respiratory gating, to provide some examples, to improve the image quality of the anatomical images. The prospective gating technique utilizes one or more physiological events of the biological organism to trigger the example MRI system to image the biological organism at specific times to improve the image quality of the anatomical images. However, the magnetic fields and/or the radio frequency waves can interfere with the prospective gating technique. As to be described in further detail below, the example MRI system compensates for the interference introduced by the magnetic fields and/or the radio frequency waves.

Example Magnetic Resonance Imaging (MRI) System

FIG. 1 graphically illustrates a simplified block diagram of an example magnetic resonance imaging (MRI) system in accordance with some example embodiments of the present disclosure. In the example embodiment illustrated in FIG. 1, an imaging system 100 represents a magnetic resonance imaging (MRI) system that uses magnetic fields and radio frequency waves to generate anatomical images of a biological organism, such as a human body, to provide an example. Although the imaging system 100 is described in FIG. 1 as being a magnetic resonance imaging (MRI) system, those skilled in the relevant art(s) will recognize that the teachings herein are similarly applicable to other types of imaging systems, such as computed tomography (CT) imaging systems, computerized axial tomography (CAT) imaging systems, and/or positron emission tomography (PET) imaging systems, to provide some examples, without departing from the spirit and scope of the present disclosure. As illustrated in FIG. 1, the imaging system 100 includes a patient transport table 102, an imaging machine 104, an MRI computer control system 106, an administrative workstation 108, a gating signal transmitter 110, and a gating signal receiver 112. Although the imaging machine 104 is illustrated in FIG. 1 as being a standard imaging machine having a long cylinder with a narrow tube in the center, also referred to as a bore, those skilled in the relevant art(s) will recognize that the teachings herein are similarly applicable to other types of imaging machines, such as short-bore imaging machines, open imaging machines having bores with openings, and/or wide bore imaging machines, to provide some examples, without departing from the spirit and scope of the present disclosure.

The patient transport table 102 positions a patient 116 on the patient transport table 102 into the imaging machine 104. In some embodiments, the patient transport table 102 can be adjustable in three-dimensions, for example, elevation, pitch, roll, and/or yaw, to slide the patient into the imaging machine 104. As illustrated in FIG. 1, the patient 116 is positioned onto the patient transport table 102 that can be adjusted to position, for example, slide, the patient 116 into the imaging machine 104 for imaging.

The imaging machine 104 performs magnetic resonance imaging (MRI) imaging of the patient 116 using a combination of magnetic fields and radio frequency waves. In the example embodiment illustrated in FIG. 1, the imaging machine 104 generates an intense, stable, primary magnetic field, for example, between approximately 0.5 tesla (T) to approximately 3.0 T. In some embodiments, the primary magnetic field surrounds the patient 116 once the patient 116 is positioned into the imaging machine 104. In these embodiments, the primary magnetic field can cause subatomic particles, for example, protons, within tissues of the patient 116 to align themselves with the primary magnetic field. In these embodiments, the protons are often protons of hydrogen atoms that are naturally abundant in biological organisms, particularly in water and fat cells within these organisms.

The imaging machine 104 can generate one or more variable, secondary magnetic fields, for example, gradient magnetic field pulses, which slightly distort the primary magnetic field to allow different spatial locations, for example, slices, of the patient 116 to be imaged. These gradient magnetic field pulses can be directed toward a specific spatial location, or slice, of the patient 116 to image the specific spatial location. In some embodiments, the gradient magnetic field pulses can cause frequency variations in the specific spatial location, or slice, of the patient 116 so the specific spatial location can be excited by the radio frequency waves.

The imaging machine 104 can generate the radio frequency waves, for example, radio frequency pulses, which are directed toward the patient 116 to image the specific spatial location of the patient 116. In some embodiments, the sub-atomic particles within the tissues of the patient 116 within the specific spatial location absorb the radio frequency pulses. In these embodiments, the sub-atomic absorb energy from the radio frequency pulses that causes these particles rotate away from the primary magnetic field. In these embodiments, the sub-atomic absorb rotate away from the primary magnetic field when the frequency of the radio frequency pulses matches a precessional frequency at which these sub-atomic particles rotate. In these embodiments, the imaging machine 104 can deactivate the radio frequency pulses to cause these sub-atomic particles to slowly return to their alignment within the primary magnetic field which releases the energy absorbed from the radio frequency pulses. Generally, the amount of energy released by the sub-atomic particles is related to the chemical nature of the tissues of the patient 116. In some embodiments, the imaging machine 104 can detect the amount of energy released, for example, using a coil (not illustrated in FIG. 1) that is placed around the patient 116. In these embodiments, the imaging machine 104 can thereafter transform the detected energy released into electrical signals to provide image data signals indicative of the compositions of the tissues of the patient 116 within the specific spatial location to the control system 106.

The control system 106 can include one or more computing devices, such as one or more desktop computers, one or more rackmount computers, one or more computer hardware servers, and/or any other computing device having one or more processors that will be recognized by those skilled in the relevant art(s) without departing from the spirit and scope of the present disclosure. Although not illustrated in FIG. 1, the control system 106 can include, or be connected to, other hardware components for operating the imaging machine 104, such as one or more waveform generators, one or more amplifiers, one or more radio frequency transmitters, one or more radio frequency receivers, one or more digital to analog converters (DACs), one or more analog to digital converters (ADCs), one or more mixers, one or more power supplies, one or more water pumps, one or more pumps for super cooling fluids, such as liquid helium or liquid nitrogen, to provide some examples, and/or one or more super cooling fluid storage tanks, to provide some examples. These other hardware components are well-known by those skilled in the relevant art(s) and will not be discussed in further detail.

In some embodiments, the control system 106 can configure the gradient magnetic field pulses and/or the radio frequency pulses to be applied by the imaging machine 104 to image the patient 116 to acquire the image data signals. For example, the control system 106 can configure the gradient magnetic field pulses to excite specific spatial locations, for example, slices, of the patient 116 to be imaged and/or can configure various radio frequency pulses to image these specific spatial locations. In some embodiments, the control system 106 can control one or more waveform generators that generate the gradient magnetic field pulses and/or the radio frequency pulses and/or one or more amplifiers that strengthen the gradient magnetic field pulses and/or the radio frequency pulses. In these embodiments, the one or more waveform generators and/or the one or more amplifiers can be implemented as standalone, or discrete devices, and/or can be incorporated within or coupled to the control system 106.

In some embodiments, the control system 106 can analyze the image data signals provided by the imaging machine 104 to generate the anatomical images of the patient 116. In these embodiments, the anatomical images of the patient 116 graphically illustrate the compositions of the tissues of the patient 116 within the spatial locations. In some embodiments, the control system 106 can transform the image data signals using a mathematical transformation, for example, a Fourier transformation, to mathematically transform the image data signals into the anatomical images of the patient 116. In these embodiments, the Fourier transform allows the image data signals to be decomposed into a combination of sine waves of different frequencies, phases, and amplitudes that can be used to generate the anatomical images of the patient 116 as will be recognized by those skilled in the relevant art(s) without departing from the spirit and scope of the present disclosure.

The administrative workstation 108 can display one or more of the anatomical images of the patient 116 that are generated by the control system 106. In some embodiments, the administrative workstation 108 can further process one or more of the anatomical images of the patient 116 to change their characteristics, such as windowing and/or magnification, to provide some examples, to reformat one or more of the anatomical images of the patient 116, or to display specific views of the patient 116 from the anatomical images of the patient 116. In some embodiments, the administrative workstation 108 can be situated within a specialized location within the imaging system 100 that is electrically and/or magnetically isolated from the imaging machine 104 and/or the control system 106.

In the example embodiment illustrated in FIG. 1, the image quality, for example, the contrast and spatial resolution, of the anatomical images generated by the control system 106 can be less than optimal because of one or more physiological events of the patient 116, for example, the heartbeat and/or the respiration of the patient 116. In the example embodiment illustrated in FIG. 1, the control system 106 can implement one or more gating techniques, such as a prospective gating technique, for example, cardiac gating and/or respiratory gating, and/or a retrospective gating technique to improve the image quality of the anatomical images. The one or more gating techniques utilize the one or more physiological events of the patient 116 to trigger the imaging machine 104 to image the patient 116 at specific times to improve the image quality of the anatomical images, for example, to improve the temporal resolution of the anatomical images and/or to minimize imaging artifacts caused by the one or more physiological events of the patient 116. For example, the control system 106, when implementing the cardiac gating, can trigger the imaging machine 104 to image the patient 116 during a specific portion of the cardiac cycle, such as diastole when the ventricles of the heart are passively filling. As another example, the control system 106, when implementing the respiratory gating, can predict the phase of the breathing cycle of the patient 116 while the patient 116 breathes freely which can improve the contrast and spatial resolution of the anatomical images.

As illustrated in FIG. 1, one or more sensors 118 can be placed onto the patient 116 to provide one or more physiological event signals that can be used to measure the one or more physiological events of the patient 116. In some embodiments, the one or more sensors 118 can include one or more heart activity electrodes that are placed on the chest, the arms, and/or the legs of the patient 116 to provide one or more electrocardiogram (ECG) signals with their characteristic P waves, Q waves, R waves, S waves, T waves and U waves, and/or associated QRS complexes in combination with any other signal deflections represented in a given waveform. In these embodiments, the control system 106 can measure the electrical activity of the heart of the patient 116 based upon the one or more ECG signals as will be recognized by those skilled in the relevant art(s) without departing from the spirit and scope of the present disclosure. In some embodiments, the one or more sensors 118 can include a pulse oximeter that is placed on one of the fingers of the patient 116 to provide a photoplethysmogram (PPG) signal. In these embodiments, the control system 106 can measure the pulse rate of the heart of the patient 116 based upon the PPG signal as will be recognized by those skilled in the relevant art(s) without departing from the spirit and scope of the present disclosure. In some embodiments, the one or more sensors 118 can include a respiratory sensor, such as a thoracic belt, bellows, or cushion, to provide some examples, that is placed around the abdomen and/or the chest of the patient 116 to provide a respiratory (RESP) signal. In these embodiments, the control system 106 can measure the respiratory expansion of the abdomen and/or the chest of the patient 116 based upon the RESP signal as will be recognized by those skilled in the relevant art(s) without departing from the spirit and scope of the present disclosure. In the example embodiment illustrated in FIG. 1, the control system 106 can utilize the one or more ECG signals, the PPG signal, and/or the RESP signal to trigger the imaging machine 104 according to various prospective gating techniques that will be recognized by those skilled in the relevant art(s) without departing from the spirit and scope of the present disclosure.

The one or more physiological event signals can be transported to the gating signal transmitter 110 using one or more leadwires 120. In some embodiments, the one or more leadwires 120 can be implemented as simple conductors of tin, copper, and/or silver, to provide some examples, to more complicated conductors that are shielded using polyvinyl chloride (PVC), polyethylene (PE), polypropylene (PP), thermoplastic elastomer (TPE), thermoplastic rubber (TPR), thermoplastic polyurethane (TPU), fluorinated ethylene-propylene (FEP), and/or ethylene-tetrafluoroethylene (ETFE) to provide some examples. In the example embodiment illustrated in FIG. 1, the gradient magnetic field pulses and/or the radio frequency pulses used by the imaging machine 104 can interfere with the one or more physiological event signals. In some embodiments, the gradient magnetic field pulses and/or the radio frequency pulses can introduce gradient pulse interference and/or signal offsets, for example, common mode offsets, into the one or more physiological event signals. In these embodiments, the gradient magnetic field pulses can couple onto the one or more leadwires 120 as the one or more physiological event signals are being transported by the one or more leadwires 120. In these embodiments, the radio frequency pulses can be demodulated into common mode interference that can impact, for example, power rails and/or high impedance circuit nodes of the imaging system 100 to introduce unwanted noise, such as amplitude modulated (AM) noise, to provide an example, into the one or more physiological event signals.

In the example embodiment illustrated in FIG. 1, the gating signal transmitter 110 compensates for the interference introduced by the gradient magnetic field pulses and/or the radio frequency pulses onto the one or more physiological event signals. In some embodiments, the gating signal transmitter 110 can process the one or more physiological event signals to reduce the interference introduced by the gradient magnetic field pulses and/or the radio frequency pulses, such as gradient pulse interference, and/or signal offsets, to provide some examples, onto the one or more physiological event signals. In some embodiments, as to be described in further detail below, the gating signal transmitter 110 can compensate for the gradient pulse interference. In these embodiments, the gating signal transmitter 110 can use a non-linear separation technique, such as a median filter, mean filter, wavelet or ranklet filter, phase detector, frequency mixer, oscillator, modulator, or any combination thereof, to provide a few non-limiting examples, in order to reduce the gradient pulse interference. In some embodiments, as to be described in further detail below, the gating signal transmitter 110 can compensate for the signal offsets. In these embodiments, the gating signal transmitter 110 can evaluate an interference cost function, which is to be described in further detail below, to reduce the signal offsets. As illustrated in FIG. 1, the gating signal transmitter 110 provides the one or more physiological event signals to the gating signal receiver 112 for delivery to the control system 106. In some embodiments, the gating signal receiver 112 can be implemented as a standalone, or a discrete device, as illustrated in FIG. 1 and/or can be incorporated within or coupled to the control system 106. Example embodiments of the gating signal transmitter 110 and the gating signal receiver 112 are to be described in further detail below.

Example Physiological Event Signal Within the Example MRI Imaging System

FIG. 2 graphically illustrates various signals within the example MRI imaging system in accordance with some example embodiments of the present disclosure. As described above, a heart activity electrode can be placed on the chest, the arm, and/or the leg of a patient, such as the patient 116 as described above in FIG. 1, to provide an electrocardiogram (ECG) signal 200 as illustrated in FIG. 2. The ECG signal 200, as illustrated in FIG. 2, represents a clean ECG signal that is free from interference from the gradient magnetic field pulses and/or the radio frequency pulses being used to image the patient. In the example embodiment illustrated in FIG. 2, the interference from the gradient magnetic field pulses and/or the radio frequency pulses are graphically illustrated as an unwanted noise signal 210. As illustrated in FIG. 2, the unwanted noise signal 210 can include a slow gradient interference pulse 212 that results from the switching of the gradient magnetic field pulses and a fast gradient interference pulse 214 that results from the switching of the radio frequency pulses. In some embodiments, the slow gradient interference pulse 212 and/or the fast gradient interference pulse 214 can introduce the gradient pulse interference and/or the signal offsets into the ECG signal 200 in a substantially similar manner as described above in FIG. 1 to provide a noisy ECG signal 220. In some embodiments, the noisy ECG signal 220 can include fast pulses, for example, between approximately 0.1 milliseconds (ms) and approximately four (4) ms in duration and/or long signal offsets, for example, between approximately fifty (50) milliseconds (ms) and approximately two hundred (200) ms that are superimposed onto the ECG signal 200.

Example Gating Transmitter That can be Implemented Within the Example MRI Imaging System FIG. 3 graphically illustrates a block diagram for an example gating transmitter that can be implemented within the example MRI imaging system in accordance with some example embodiments of the present disclosure. The gradient magnetic field pulses and/or the radio frequency pulses used by an imaging machine, such as the imaging machine 104 as described above in FIG. 1, can interfere with one or more physiological event signals that are used to measure one or more physiological events of a patient in a substantially similar manner as described above in FIG. 1 and FIG. 2. As to be described in further detail below, the gating signal transmitter 300 can compensate for the interference introduced by the gradient magnetic field pulses and/or the radio frequency pulses onto the one or more physiological event signals. As illustrated in FIG. 3, the gating signal transmitter 300 can include an analog processing circuitry 302, analog-to-digital (ADC) converters 304, digital processing circuitry 306, and/or a communication transmitter 308. In some embodiments, the gating signal transmitter 300 can represent an example embodiment of the gating signal transmitter 110 as described above in FIG. 1.

The analog processing circuitry 302 can process, for example, through amplification and/or signal conditioning, noisy physiological event signals 350 in the analog signal domain to provide processed physiological event signals to the ADC 304. As illustrated in FIG. 3, the noisy physiological event signals 350 can include an electrocardiogram (ECG) signal 350.1, a photoplethysmogram (PPG) signal 350.2, and a provide a respiratory (RESP) signal 350.3. In some embodiments, the ECG signal 350.1, the PPG signal 350.2, and/or the RESP signal 350.3 can be generated by placing one or more sensors, such as the one or more sensors 118 as described above in FIG. 1, onto a patient, such as the patient 116 as described above in FIG. 1, in a substantially similar manner as described above in FIG. 1. In these embodiments, one or more leadwires, such as the one or more leadwires 120 as described above in FIG. 1, can be connected between the one or more sensors and the analog processing circuitry 302 to transport the ECG signal 350.1, the PPG signal 350.2, and/or the RESP signal 350.3 to the analog processing circuitry 302. In some embodiments, the ECG signal 350.1 can be characterized as being a relatively fast electrical signal, the PPG signal 350.2 can be characterized as being a relatively slow electrical signal, and the RESP signal 350.3 can be characterized as being an optical signal. In these embodiments, the PPG signal 350.2 and/or the RESP signal 350.3 can be assumed to be not impacted by the interference from the gradient magnetic field pulses and/or the radio frequency pulses as compared to the ECG signal 350.1. As such, the gating signal transmitter 300 compensates for the interference from the gradient magnetic field pulses and/or the radio frequency pulses that is introduced into the ECG signal 350.1 as to be described in further detail below. However, those skilled in the relevant art(s) will recognize that the teachings described herein to compensate for the interference from the gradient magnetic field pulses and/or the radio frequency pulses that introduced into the ECG signal 350.1 are equally applicable to compensate for the interference from the gradient magnetic field pulses and/or the radio frequency pulses that is introduced into the PPG signal 350.2 and/or the RESP signal 350.3 without departing from the spirit and scope of the present disclosure. In some embodiments, the ECG signal 350.1, the PPG signal 350.2, and/or the RESP signal 350.3 can represent one or more differential signals.

The analog processing circuitry 302 includes an ECG analog front end (AFE) 310.1, a PPG AFE 310.2, and a RESP AFE 310.3 to receive the ECG signal 350.1, the PPG signal 350.2, and the RESP signal 350.3, respectively. In the example embodiment illustrated in FIG. 3, the ECG AFE 310.1, the PPG AFE 310.2, and the RESP AFE 310.3 can process, for example, through amplification and/or signal conditioning, the ECG signal 350.1, the PPG signal 350.2, and the RESP signal 350.3, respectively, in the analog signal domain. In some embodiments, the ECG AFE 310.1, the PPG AFE 310.2, and/or the RESP AFE 310.3 can include a signal converter, such as an optical-to-electrical converter, to provide an example, to convert the ECG signal 350.1, the PPG signal 350.2, and/or the RESP signal 350.3 into electrical signals. In some embodiments, the ECG AFE 310.1, the PPG AFE 310.2, and the RESP AFE 310.3 can include various amplifiers, such as operational amplifiers (op-amps), and/or differential amplifiers, to provide some examples, to amplify the ECG signal 350.1, the PPG signal 350.2, and the RESP signal 350.3, respectively. In some embodiments the ECG AFE 310.1, the PPG AFE 310.2, and the RESP AFE 310.3 can include various filters, for example, low-pass filters, band-pass filters, high-pass filters, and/or anti-aliasing filters, to provide some examples, to condition the ECG signal 350.1, the PPG signal 350.2, and the RESP signal 350.3, respectively.

In some embodiments, the ECG AFE 310.1, the PPG AFE 310.2, and/or the RESP AFE 310.3 can process the ECG signal 350.1, the PPG signal 350.2, and the RESP signal 350.3, respectively, in the analog signal domain differently from one another. For example, the ECG AFE 310.1 can include an anti-aliasing filter having a bandwidth of approximately one (1) kiloHertz (kHz) that is coupled to an amplifier having a gain of one, also referred to as a buffer amplifier. The one (1) kHz bandwidth of the anti-aliasing filter is sufficient to capture the interference from the gradient magnetic field pulses and/or the radio frequency pulses that is introduced into the ECG signal 350.1. As another example, the PPG AFE 310.2 can include a first order bandpass filter having a bandwidth between approximately 500 Hertz (Hz) and approximately 10 kHz that is coupled to an amplifier having a gain of approximately 1000 that is coupled to a third order low pass filter having a bandwidth of approximately twelve (12) Hz. As a further example, the RESP AFE 310.3 can include a first order low pass filter having a bandwidth of approximately seven (7) Hz that is coupled to an amplifier having a gain of approximately 1000 that is coupled to a second order low pass filter having a bandwidth of approximately five (5) Hz. The seven (7) Hz bandwidth of the first order low pass filter and the five (5) Hz bandwidth of the second order low pass filter is sufficient to remove the interference from the gradient magnetic field pulses and/or the radio frequency pulses that is introduced into the RESP signal 350.3. In some embodiments, the ECG AFE 310.1, the PPG AFE 310.2, and the RESP AFE 310.3 can include various radio-frequency interference (RFI) and/ or electrostatic discharge (ESD) circuitries to protect the ECG AFE 310.1, the PPG AFE 310.2, and the RESP AFE 310.3 from RFI and/or ESD events. In these embodiments, the RFI and/or the ESD circuitries can be implemented using analog circuits and/or circuitries to protect the ECG AFE 310.1, the PPG AFE 310.2, and the RESP AFE 310.3 from the RFI and/or ESD events that will be apparent to those skilled in the relevant art(s) without departing from the spirit and scope of the present disclosure.

The ADC 304 converts the processed physiological event signals received from the analog processing circuitry 302 from the analog signal domain to the digital signal domain to provide digital physiological event signals to the digital processing circuitry 306. In the example embodiment illustrated in FIG. 3, the ADC 304 includes an ADC 312.1, an ADC 312.2, and an ADC 312.3. In some embodiments, the ADC 312.1, the ADC 312.2, and/or the ADC 312.3 can be implemented as standalone, or discrete devices, and/or can be incorporated within or coupled to the digital processing circuitry 306. As to be described in further detail below, the digital processing circuitry 306 can be implemented using a specialized processor chip, such as a digital signal processor (DSP) or an application-specific integrated circuit (ASIC) to provide some examples. In some embodiments, the specialized processor chip can include on-chip ADCs. In these embodiments, the ADC 312.1, the ADC 312.2, and/or the ADC 312.3 can be implemented as discrete devices within the gating signal transmitter 300 and/or using the on-chip ADCs of the specialized processor chip.

The ADC 312.1, the ADC 312.2, and the ADC 312.3 convert a processed ECG signal provided by the ECG AFE 310.1, a processed PPG signal provided by the PPG AFE 310.2, and a processed RESP signal provided by the RESP AFE 310.3, respectively, from the analog signal domain to the digital signal domain. In some embodiments, the ADC 312.1, the ADC 312.2, and/or the ADC 312.3 can be implemented as wideband ADCs having a sampling rate of, for example, approximately 8 kHz, to capture the interference that is introduced into the ECG signal 350.1, the PPG signal 350.2, and the RESP signal 350.3, respectively. In the example embodiment illustrated in FIG. 3, the ADC 312.1 can be implemented as the wideband ADC having a faster sampling rate when compared to the sampling rate, for example, approximately 1 kHz, of the ADC 312.2 and the ADC 312.3. In some embodiments, the ADC 312.1, the ADC 312.2, and/or the ADC 312.3 can be implemented with different resolutions. For example, the ADC 312.1 can be implemented with a twenty-four (24) bit resolution when compared to the resolutions, for example, twelve (12) bit resolution, of the ADC 312.2 and the ADC 312.3. In some embodiments, the interference from the gradient magnetic field pulses and/or the radio frequency pulses introduced into the ECG signal 350.1 can be quite large when compared to the ECG signal 350.1 itself. In these embodiments, the higher resolution of the ADC 312.1, when compared to the ADC 312.2 and the ADC 312.3, allows the ADC 312.1 to sufficiently sample the ECG signal 350.1 to capture the interference from the gradient magnetic field pulses and/or the radio frequency pulses that is introduced into the ECG signal 350.1.

The digital processing circuitry 306 can process, for example, through signal conditioning, the digital physiological event signals received from the ADC 304 in the digital signal domain to provide clean physiological event signals to the communication transmitter 308. In the example embodiment illustrated in FIG. 3, the digital processing circuitry 306 includes a gradient offset filter 314, a gradient rejection filter 316, a digital filter 318, a downsampler 320, and combination circuitry 322. In some embodiments, the gradient offset filter 314, the gradient rejection filter 316, the digital filter 318, the downsampler 320, and the combination circuitry 322 can be implemented as standalone, or discrete devices, within the digital processing circuitry 306, and/or can be incorporated within or coupled to the specialized processor chip as described above.

In some embodiments, as described above, the PPG signal 350.2 and/or the RESP signal 350.3 can be assumed to be not impacted by the interference from the gradient magnetic field pulses and/or the radio frequency pulses as compared to the ECG signal 350.1. In these embodiments, a digital PPG signal and a digital RESP signal received from the ADC 312.2 and the ADC 312.3, respectively, represent clean signals that are not significantly impacted from the interference from the gradient magnetic field pulses and/or the radio frequency pulses. In these embodiments, the digital processing circuitry 306 can process, for example, through signal conditioning, a digital ECG signal received from the ADC 312.1 in the digital signal domain to provide a clean ECG signal that is free from the interference from the gradient magnetic field pulses and/or the radio frequency pulses as to be described in further detail below.

The gradient offset filter 314 can compensate for signal offsets, for example, common mode offsets, introduced into the ECG signal 350.1 by the gradient magnetic field pulses and/or the radio frequency pulses. In some embodiments, the gradient offset filter 314 can process samples of the digital ECG signal provided by the ADC 312.1 in the digital signal domain to reduce the signal offsets introduced into the ECG signal 350.1 by the gradient magnetic field pulses and/or the radio frequency pulses. In some embodiments, the gradient offset filter 314 accumulates samples of the digital ECG signal provided by the ADC 312.1 over an interference time window. In these embodiments, the interference time window can have a duration of, for example, approximately two (2) ms. In some embodiments, the gradient offset filter 314 evaluates the samples of the digital ECG signal provided by the ADC 312.1 that are accumulated during each time interference window in accordance with an interference cost function to identify a sample during each time interference window that best represents the ECG signal 350.1. In these embodiments, the interference cost function can evaluate, for each time interference window, volatilities of the samples of the digital ECG signal provided by the ADC 312.1, changes in direction of the samples of the digital ECG signal provided by the ADC 312.1, and/or offsets between the samples of the digital ECG signal provided by the ADC 312.1 to identify the sample having the least cost that best represents the ECG signal 350.1 without the interference from the gradient magnetic field pulses and/or the radio frequency pulses. An example embodiment of the gradient offset filter 314 is to be further described below in FIG. 4.

The gradient rejection filter 316 can compensate for the gradient pulse interference introduced into the ECG signal 350.1 by the gradient magnetic field pulses and/or the radio frequency pulses. In some embodiments, the gradient rejection filter 316 can process samples of a digital ECG signal provided by the gradient offset filter 314 in the digital signal domain to reduce the gradient pulse interference introduced into the ECG signal 350.1 by the gradient magnetic field pulses and/or the radio frequency pulses. In some embodiments, the gradient rejection filter 316 can use a non-linear separation technique, such as a digital median filter, to provide an example, on samples of the digital ECG signal provided by the gradient offset filter 314 to compensate for the gradient pulse interference. In some embodiments, the gradient pulse interference can be characterized as being impulse noise, such as salt-and-pepper or speckle noise, for example, that can be compensated for by the gradient rejection filter 316. In some embodiments, for example, using a median filter, the median filter may analyze neighboring samples of a sample from among the samples of ECG signal provided by the gradient offset filter 314, also referred to as median window, to determine a median value of these samples. In these embodiments, the median filter may substitute the median value of the median window for the sample(s). The median filter may iteratively advance the median window to other samples of ECG signal provided by the gradient offset filter 314 to compensate for the gradient pulse interference.

The digital filter 318 further filters a digital ECG signal received from the gradient rejection filter 316. In some embodiments, the digital filter 318 can be characterized as being a linear filter, a causal filter, a non-causal filter, a time-invariant filter, a stable filter, an unstable filter, a finite impulse response (FIR) filter, and/or any other type of digital filter that will be apparent to those skilled in the relevant art(s) without departing from the spirit and scope of present disclosure. The digital filter 318 can include a digital low-pass filter, a digital high-pass filter, a digital band-pass filter, a digital band-stop filter, and/or any other digital filter topology that will be apparent to those skilled in the relevant art(s) without departing from the spirit and scope of present disclosure. In some embodiments, the digital filter 318 can remove high-frequency noise, for example, greater than 150 Hz, from the digital ECG signal received from the gradient rejection filter 316, such as impulse noise, flicker noise, and/or white noise, to provide some examples. In some embodiments, the digital filter 318 is optional.

The downsampler 320 samples the digital ECG signal received from the gradient rejection filter 316 or a digital ECG signal received from the digital filter 318 to a sampling rate of the ADC 312.1 and/or the ADC 312.2. In some embodiments, the downsampler 320 downsamples the sampling rate of the digital ECG signal received from the gradient rejection filter 316 or the digital ECG signal received from the digital filter 318, for example, eight (8) kHz, to match the sampling rate of the digital PPG signal received from the ADC 312.2 and/or the digital RESP signal received from the ADC 312.3, for example, one (1) kHz. In some embodiments, the downsampler 320 is optional, for example, when the sampling rates of the ADC 312.1, the ADC 312.2, and the ADC 312.3 are the same.

The combination circuitry 322 combines the digital ECG signal received from the gradient rejection filter 316, the digital filter 318, or the downsampler 320, the digital PPG signal received from the ADC 312.2 and the digital RESP signal received from the ADC 312.3 to provide a physiological event signal for transmission. In some embodiments, the combination circuitry 322 can be implemented as a digital adder, such as a full adder, a half adder, a ripple-carry adder, carry-lookahead adder, a carry-save adder, a quantum full adder, and/or any other suitable digital circuit that is capable of combine digital signals that will be apparent to those skilled in the relevant art(s) without departing from the spirit and scope of the present disclosure.

The communication transmitter 308 formats the physiological event signal from the combination circuitry 322 to provide clean physiological event signals 352 for transmission to a communication receiver, such as the gating signal receiver 112 as described above in FIG. 1. In some embodiments, the communication transmitter 308 can communicate the clean physiological event signals 352 over a wireless communication network, a wireline communication network, and/or any combination thereof that will be apparent to those skilled in the relevant art(s) without departing from the spirit and scope of the present disclosure. In these embodiments, the wireless communication network can be compliant with, for example, a version of an Institute of Electrical and Electronics Engineers (I.E.E.E.) 802.11 communication standard, for example, 802.11a, 802.11b/g/n, 802.11h, and/or 802.11ac, which are collectively referred to as Wi-Fi, a version of a Bluetooth communication standard, and/or or any other wireless communication standard or protocol that will be apparent to those skilled in the relevant art(s) without departing from the spirit and scope of the present disclosure. In these embodiments, the wireline communication network can be compliant with, for example, a version of a standard or protocol such as IEEE 802.10, also referred as Ethernet, and/or or any other wireline communication standard or protocol that will be apparent to those skilled in the relevant art(s) without departing from the spirit and scope of the present disclosure.

Example Gradient Offset Filter That can be Implemented Within the Example Gating Transmitter FIG. 4 graphically illustrates a block diagram for an example gradient offset filter that can be implemented within the example gating transmitter in accordance with some example embodiments of the present disclosure. The gradient magnetic field pulses and/or the radio frequency pulses used by an imaging machine, such as the imaging machine 104 as described above in FIG. 1, can interfere with one or more physiological event signals that are used to measure one or more physiological events of a patient in a substantially similar manner as described above in FIG. 1 through FIG. 3. In some embodiments, the gradient magnetic field pulses and/or the radio frequency pulses can introduce signal offsets, for example, common mode offsets, into the one or more physiological event signals. In these embodiments, the signal offsets can between approximately fifty (50) milliseconds (ms) and approximately two hundred (200) ms. As to be described in further detail below, a gradient offset filter 400 can compensate for the signal offsets introduced by the gradient magnetic field pulses and/or the radio frequency pulses onto the one or more physiological event signals. In some embodiments, the gradient offset filter 400 can evaluate an interference cost function to identify samples of the one or more physiological event signals that best represents the one or more physiological event signals without the interference from the gradient magnetic field pulses and/or the radio frequency pulses. In these embodiments, the interference cost function can evaluate, volatilities of samples of the one or more physiological event signals, changes in direction of the samples of the one or more physiological event signals, and/or offsets between the samples of the one or more physiological event signals to identify a sample that best represents the one or more physiological event signals without the interference from the gradient magnetic field pulses and/or the radio frequency pulses.

As illustrated in FIG. 4, the gradient offset filter 400 can include a sample queue 402, a statistical module 404, digital adder circuits 406 through 410, a monotonicity module 412, a cost function module 414, and a cost analysis module 416. Herein references to a "module" shall be understood to include at least one of software, firmware, hardware, such as one or more circuits, microchips, and/or electronic devices, to provide some examples, and/or any combination thereof. In some embodiments, the sample queue 402, the statistical module 404, the digital adder circuits 406 through 410, the monotonicity module 412, the cost function module 414, and/or the cost analysis module 416 can be implemented as discrete devices within the gradient offset filter 400 and/or integrated within the specialized processor chip as described above. In some embodiments, the gradient offset filter 400 can represent an example embodiment of the gradient offset filter 314 as described above in FIG. 3.

The sample queue 402 accumulates samples of a digital ECG signal 450, such as the digital ECG signal provided by the ADC 312.1 as described above in FIG. 3 to provide an example. Although the discussion of FIG. 4 to follow is to be described in terms of ECG signals, those skilled in the relevant art(s) will recognize that the teachings herein are equally applicable to compensate for the signal offsets introduced by the gradient magnetic field pulses and/or the radio frequency pulses onto PPG signals and/or RESP signals without departing from the spirit and scope of the present disclosure. In the example embodiment illustrated in FIG. 4, the sample queue 402 accumulates N-samples of the digital ECG signal 450 over an interference time window, for example, a group of samples of the digital ECG signal provided by the ADC 312.1. In these embodiments, the interference time window can have a duration of, for example, approximately two (2) ms. In some embodiments, the sample queue 402 can be implemented as one or more first in, first out (FIFO) queues, one or more circular buffers, and/or any other suitable architecture that will be apparent to those skilled in the relevant art(s) without departing from the spirit and scope of the present disclosure.

The statistical module 404 calculates one or more statistical measurements of the samples of the digital ECG signal 450 that are accumulated in the sample queue 402. In some embodiments, the one or more statistical measurements can include a moving mean, a moving median, a moving average, a moving mean square, a moving root mean square, a moving variance, and/or a moving norm, to provide some examples of the samples of the digital ECG signal 450 that are accumulated in the sample queue 402. In some embodiments, the statistical module 404 calculates one or more statistical measurements of the samples of the digital ECG signal 450 that are accumulated in the sample queue 402 during the time interference time window.

The digital adder circuits 406 through 410 combine various samples of the digital ECG signal 450 that are accumulated in the sample queue 402 and/or the one or more statistical measurements provided by the statistical module 404 to provide various input signals to the monotonicity module 412 and/or the cost function module 414. In the example embodiment illustrated in FIG. 4, the digital adder circuit 406 subtracts an $i^{th}$ sample of the digital ECG signal 450 that is accumulated in the sample queue 402 from the one or more statistical measurements, such as a moving average, to provide an example, to provide an offset signal (OFFSET) to the cost function module 414. In some embodiments, the offset signal represents a deviation, or offset, of the $i^{th}$ sample from the one or more statistical measurements, such as the moving average, to provide an example, provided by the statistical module 404. In the example embodiment illustrated in FIG. 4, the digital adder circuit 408 subtracts an $(i+1)^{th}$ sample of the digital ECG signal 450 that is accumulated in the sample queue 402 from the $i^{th}$ sample of the digital ECG signal 450 and the digital adder circuit 410 subtracts an $(i+2)^{th}$ sample of the digital ECG signal 450 that is accumulated in the sample queue 402 from the $(i+1)^{th}$ sample of the digital ECG signal 450 to provide a first derivative signal (DV_0) and a second derivative signal (DV_1), respectively, to the monotonicity module 412 and the cost function module 414. In some embodiments, the first derivative signal and the second derivative signal can be used to indicate trends of the samples of the digital ECG signal 450 that are accumulated in the sample queue 402, for example, whether these samples are increasing, decreasing, and/or changing direction.

The monotonicity module 412 determines the monotonicity of the samples of the digital ECG signal 450 that are accumulated in the sample queue 402, namely, whether these samples are increasing, decreasing, and/or changing direction. In some embodiments, the interference time window can be of sufficient duration to capture the interference that is introduced onto the digital ECG signal 450 by multiple gradient magnetic field pulses and/or radio frequency pulses. In these embodiments, when the $i^{th}$ sample through the $(i+2)^{th}$ sample of the digital ECG signal 450 are decreasing, these samples are indicative of a single gradient magnetic field pulse and/or radio frequency pulse. In these embodiments, when the $i^{th}$ sample through the $(i+2)^{th}$ sample of the digital ECG signal 450 are changing direction, these samples are indicative of multiple gradient magnetic field pulses and/or radio frequency pulses. In the example embodiment illustrated in FIG. 4, when the sign of the first derivative signal (DV_0) is not equal to the sign of the second derivative signal (DV_1), the monotonicity module 412 determines that $i^{th}$ sample through the $(i+2)^{th}$ sample of the digital ECG signal 450 are changing direction. As illustrated in FIG. 4, the monotonicity module 412 provides a monotonicity signal (MONO) to the cost function module 414 having different integer values based upon whether the $i^{th}$ sample through the $(i+2)^{th}$ sample of the digital ECG signal 450 are changing direction. In some embodiments, the monotonicity module 412 sets the monotonicity signal to a relatively large integer value, for example, ten (10), when the $i^{th}$ sample through the $(i+2)^{th}$ sample of the digital ECG signal 450 are changing direction. In these embodiments, the relatively large integer value is selectively chosen to effectively exclude the $i^{th}$ sample of the digital ECG signal 450 from being selected as being the best representative of the digital ECG signal 450 without the interference from the gradient magnetic field pulses and/or the radio frequency pulses. In some embodiments, the monotonicity module 412 sets the monotonicity signal to a relatively small integer value, for example, one (1), when the $i^{th}$ sample through the $(i+2)^{th}$ sample of the digital ECG signal 450 are not changing direction. In these embodiments, the relatively small integer value is selectively chosen to effectively allow the $i^{th}$ sample of the digital ECG signal 450 from being selected as being the best representative of the digital ECG signal 450 without the interference from the gradient magnetic field pulses and/or the radio frequency pulses.

The cost function module 414 can implement an interference cost function that maps the $i^{th}$ sample of the digital ECG signal 450 onto a real number (WEIGHT) that represents an estimation of the difference between the digital ECG signal 450 and the digital ECG signal 450 without the interference from the gradient magnetic field pulses and/or the radio frequency pulses. In some embodiments, the interference cost function can evaluate volatilities of samples of the digital ECG signal 450, changes in direction of the samples of the digital ECG signal 450, and/or offsets between the digital ECG signal 450. In these embodiments, the interference cost function can be represented as:

$$weight=((|DV\_0|+|DV\_1|*MONO)+|offset|), \qquad (1)$$

wherein weight represents the estimation of the difference as described above, $|DV\_0|$ and $|DV\_1|$ represent absolute value of the first derivative signal and the second derivative signal, respectively, MONO represents the monotonicity signal, and $|offset|$ represents the absolute value of the offset signal. Similarly, a general cost function may be useful in some cases, to provide an illustrative example, with weighted coefficients of derivative signals, offset signals, monotonicity signals, or the like. Thus, $a*x+b*y+c*z$ may represent a cost function in which x, y, and z represent derivative, offset, and monotonicity signals, respectively, and where a, b, and c represent weights, which may have different for each signal, in some use cases.

The cost analysis module 416 analyzes the weights for the samples of the digital ECG signal 450 to identify samples of the digital ECG signal 450 that best represent the digital ECG signal 450 without the interference from the gradient magnetic field pulses and/or the radio frequency pulses. In some embodiments, the cost analysis module 416 analyzes the weights for the samples of the digital ECG signal 450 during the time interference window to identify a sample of the digital ECG signal 450 during the time interference window that best represents the digital ECG signal 450 without the interference from the gradient magnetic field pulses and/or the radio frequency pulses. In some embodiments, the cost analysis module 416 analyzes the weights for the samples of the digital ECG signal 450 to identify a sample of the digital ECG signal 450 during the time interference window having the least weight as being the best representative of the digital ECG signal 450 without the interference from the gradient magnetic field pulses and/or the radio frequency pulses during the time interference window. In these embodiments, the cost analysis module 416 accumulates the weights for the samples of the digital ECG signal 450 during the time interference window and selects the sample of the digital ECG signal 450 during the time interference window having the least weight to be the sample of the digital ECG signal 450 that best represents the digital ECG signal 450 without the interference from the gradient magnetic field pulses and/or the radio frequency pulses during the time interference window.

In some embodiments, the gradient offset filter may be implemented using a selection filter or algorithm therefor, rather than using a cost function with a sliding window. Such an algorithm, favoring selection based on derivative signals and offset criteria as opposed to retaining a best sample within a sliding window, may enable reduction of complexity in implementation as well as other benefits of efficiency and reduced computational overhead. Selection-filter algorithms may therefore be desired for implementation in certain low-power embedded systems, for example.

For an example selection filter, in a manner similar to that described elsewhere herein, an offset signal may represent a deviation, or offset, of the $i^{th}$ sample from the one or more statistical measurements, such as a moving average, that may be provided by a statistical module or equivalent. In an embodiment, a digital adder circuit or equivalent may subtract an $(i-1)^{th}$ sample, of the digital ECG signal 450 that is accumulated in a sample queue or any smaller memory, e.g., circular buffer or the like, from the $i^{th}$ sample of the digital ECG signal 450, to provide a first derivative signal (DV\_0). Further, the adder circuit or equivalent may subtract an $(i-2)^{th}$ sample, of the digital ECG signal 450 that is accumulated in the sample queue or buffer, from the $i^{th}$ sample of the digital ECG signal 450, to provide a second derivative signal (DV\_1). As with other embodiments described elsewhere herein, the first derivative signal and the second derivative signal may be useful to indicate trends of the samples of a corresponding digital ECG signal 450, for example, whether these samples are increasing, decreasing, and/or changing direction.

Thus, in some embodiments using a selection filter, a sample may be selected as an acceptable output if certain conditions are met regarding the selection criteria. For instance, an offset-reference value (REF) may be set, as well as a derivative limit (DV\_LIMIT), as predetermined values related to the selection criteria. A sample, such as the $i^{th}$ sample from the one or more statistical measurements, may be evaluated for any or all conditions specified by predetermined selection criteria. These conditions may be, to provide one example, where $|DV\_0|$ and $|DV\_1|$ are each less than DV\_LIMIT, and where an offset value, defined by a difference of the sample value and the offset-reference value (e.g., BUF[i]−REF, where 'i' references the position of the $i^{th}$ sample as stored in a buffer vector or array, BUF[]).

As a result, of performing these computations for the selection filter, outlier samples may be rejected while allowing retention of more reliable samples, while also facilitating ease of implementation and improving computational efficiency. Other benefits of this implementation and its equivalents are readily appreciated, and other implementations may be contemplated to achieve other tradeoffs within various constraints of other computing devices, e.g., embedded systems. The examples provided herewith are not intended to be exhaustive, but rather are illustrative, in a context of rejecting certain offsets, outlier values, or gradient trends in certain sample data.

Example Gating Receiver That can be Implemented Within the Example MRI Imaging System FIG. 5 graphically illustrates a block diagram for an example gating receiver that can be implemented within the example MRI imaging system in accordance with some example embodiments of the present disclosure. As to be described in further detail below, a gating signal receiver 500 can recover physiological event signals that are provided by a gating signal transmitter, such as the gating signal transmitter 110 as described above in FIG. 1. In some embodiments, the gating signal receiver 500 can generate various clocking signals, such as triggering signals, to provide an example, from these physiological event signals that can be used to synchronize the physiological event signals to one or more physiological events of a patient, for example, the heartbeat and/or the respiration of the patient. In the example embodiment illustrated in FIG. 5, the gating signal receiver 500 can include a communication receiver 502, analog processing circuitry 504, trigger generation circuitry 506, and a communication transmitter 508.

The communication receiver 502 can receive one or more physiological event signals 550 provided by the gating signal transmitter. In some embodiments, the one or more physiological event signals 550 can include a ECG signal, a PPG signal, and/or a RESP signal. In these embodiments, the communication receiver 502 can recover the ECG signal, the PPG signal, and/or the RESP signal from the one or more physiological event signals 550. In some embodiments, the communication receiver 502 can receive the one or more physiological event signals 550 over a wireless communication network, a wireline communication network, and/or any combination thereof that will be apparent to those skilled in the relevant art(s) without departing from the spirit and scope of the present disclosure. In these embodiments, the wireless communication network can be compliant with, for example, a version of a Wi-Fi communication standard, a version of a Bluetooth communication standard, and/or or any other wireless communication standard or protocol that will be apparent to those skilled in the relevant art(s) without departing from the spirit and scope of the present disclosure. In these embodiments, the wireline communication network can be compliant with, for example, a version of an Ethernet communication standard, and/or or any other wireline communication standard or protocol that will be apparent to those skilled in the relevant art(s) without departing from the spirit and scope of the present disclosure.

The analog processing circuitry 504 can process, for example, through amplification and/or signal conditioning, the one or more physiological event signals 550 in the analog signal domain to provide processed physiological event signals to the ADC 304. In some embodiments, the analog processing circuitry 504 can include one or more analog filters to parse, or separate, the ECG signal, the PPG signal, and/or the RESP signal from one another. In some embodiments, the one or more analog filters can include an analog low-pass filter, an analog high-pass filter, an analog band-pass filter, an analog band-stop filter, and/or any other analog filter topology that will be apparent to those skilled in the relevant art(s) without departing from the spirit and scope of present disclosure. For example, the one or more analog filters can include a high-pass filter having a cutoff between of approximately 0.1 Hz and a low-pass filter having a cutoff between of approximately 10 Hz to separate the ECG signal from the PPG signal, and the RESP signal. As another example, the one or more analog filters can include a high-pass filter having a cutoff between of approximately 0.05 Hz and a low-pass filter having a cutoff between of approximately 10 Hz to separate the PPG signal from the ECG signal, and the RESP signal. As a further example, the one or more analog filters can include a high-pass filter having a cutoff between of approximately 0.1 Hz and a low-pass filter having a cutoff between of approximately 3 Hz to separate the ECG signal from the PPG signal, and the RESP signal. In some embodiments, the analog processing circuitry 504 can include one or more automatic gain control (AGC) circuits to adjust the magnitudes of the ECG signal, the PPG signal, and/or the RESP signal. In these embodiments, the one or more AGC circuits can adjust the magnitudes of the ECG signal, the PPG signal, and/or the RESP signal to be substantially similar to one another. In some embodiments, the analog processing circuitry 504 can include combination circuitry to combine the ECG signal, the PPG signal, and/or the RESP signal for transmission to, for example, the MRI computer control system 106 as described above in FIG. 1.

The trigger generation circuitry 506 can process, for example, through amplification and/or signal conditioning, the one or more physiological event signals 550 in the analog signal domain to provide one or more physiological event triggering signals. In some embodiments, the trigger generation circuitry 506 can include one or more analog filters to parse, or separate, the ECG signal, the PPG signal, and/or the RESP signal from one another. In some embodiments, the one or more analog filters can include an analog low-pass filter, an analog high-pass filter, an analog band-pass filter, an analog band-stop filter, and/or any other analog filter topology that will be apparent to those skilled in the relevant art(s) without departing from the spirit and scope of present disclosure. For example, the one or more analog filters can include a band-pass filter having a bandwidth between approximately 2 Hz and approximately 30 Hz to separate the ECG signal from the PPG signal, and the RESP signal. As another example, the one or more analog filters can include a band-pass filter having a bandwidth between approximately 0.1 Hz and approximately 10 Hz to separate the PPG signal from the ECG signal, and the RESP signal. As a further example, the one or more analog filters can include a band-pass filter having a bandwidth between approximately 0.1 Hz and approximately 3 Hz to separate the ECG signal from the PPG signal, and the RESP signal. In some embodiments, the trigger generation circuitry 506 can include one or more trigger circuits to generate the one or more physiological event triggering signals from the ECG signal, the PPG signal, and/or the RESP signal. In these embodiments, the one or more physiological event triggering signals can include an ECG trigger signal and a PPG trigger signal that can be used to synchronize the ECG signal and the PPG signal, respectively, to the heartbeat of the patient as will be recognized by those skilled in the relevant art(s) without departing from the spirit and scope of the present disclosure. In these embodiments, the one or more physiological event triggering signals can include a RESP trigger signal that can be used to synchronize the RESP signal to the respiration of the patient as will be recognized by those skilled in the relevant art(s) without departing from the spirit and scope of the present disclosure. In some embodiments, the one or more trigger circuits can be characterized as converting the ECG signal, the PPG signal, and the RESP signal from the analog signal domain to provide triggering signals, or clocking signals, in the digital signal domain. In some embodiments, the trigger generation circuitry 506 can include combination circuitry to combine the ECG trigger signal, the PPG trigger signal, and/or the RESP trigger signal for transmission to, for example, the MRI computer control system 106 as described above in FIG. 1.

The communication transmitter 508 formats the ECG signal, the PPG signal, and/or the RESP signal from the analog processing circuitry 504 and/or the ECG trigger signal, the PPG trigger signal, and/or the RESP trigger signal from the trigger generation circuitry 506 for transmission to a communication receiver within or coupled to, for example, the MRI computer control system 106 as described above in FIG. 1. In some embodiments, the communication transmitter 508 can communicate these signals over a wireless communication network, a wireline communication network, and/or any combination thereof that will be apparent to those skilled in the relevant art(s) without departing from the spirit and scope of the present disclosure. In these embodiments, the wireless communication network can be compliant with, for example, a version of a Wi-Fi communication standard, a version of a Bluetooth communication standard, and/or or any other wireless communication standard or protocol that will be apparent to those skilled in the relevant art(s) without departing from the spirit and scope of the present disclosure. In these embodiments, the wireline communication network can be compliant with, for example, a version of an Ethernet communication standard, and/or or any other wireline communication standard or protocol that will be apparent to those skilled in the relevant art(s) without departing from the spirit and scope of the present disclosure. In some embodiments, the communication transmitter 508 can include a signal converter, such as an electrical-to-optical converter, to provide an example, to convert the signals from the analog processing circuitry 504 and/or the signals from the trigger generation circuitry 506 into optical signals for transmission to the communication receiver.

Example Computer System That can be Utilized to Implement Electronic Devices Within the Example MRI Imaging System FIG. 6 graphically illustrates a simplified block diagram of a computer system suitable for use with embodiments described herein according to some example embodiments of the present disclosure. The various electronic devices, for example, the MRI computer system 106, and/or the administrative workstation 108 as described above in FIG. 1, can be implemented in hardware, firmware, software, or any combination thereof. The discussion of FIG. 6 to follow describes an example computer system 610 that can be used for these electronic devices.

In the example embodiment illustrated in FIG. 6, the computer system 610 typically includes at least one processor 614 which communicates with a number of peripheral devices via bus subsystem 612. Typically, the at least processor 614 can include, or can be, any of a microprocessor, graphics processing unit, or digital signal processor, and their electronic processing equivalents, such as an Application Specific Integrated Circuit ("ASIC") or Field Programmable Gate Array ("FPGA"). As used herein, the term "processor" signifies a tangible data and information processing device that physically transforms data and information, typically using a sequence transformation (also referred to as "operations"). Data and information can be physically represented by an electrical, magnetic, optical or acoustical signal that is capable of being stored, accessed, transferred, combined, compared, or otherwise manipulated by the processor. The term "processor" can signify a singular processor and multi-core systems or multi-processor arrays, including graphic processing units, digital signal processors, digital processors or combinations of these elements. The processor can be electronic, for example, comprising digital logic circuitry (for example, binary logic), or analog (for example, an operational amplifier).

The processor(s) may also operate to a client or server, accessing or hosting any applications and/or data through any delivery paradigm, including but not limited to remote or distributed cloud computing solutions; local or on-premises software; and may support performance of the relevant operations in a "cloud computing" environment or according to any "as a service" models (e.g., software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), database as a service (DBaaS), etc.); and/or a hybrid model including any combination of the foregoing examples or other services or delivery paradigms.

By way of further example, at least some of the operations may be performed by a group of processors available at a distributed or remote system, these processors accessible via a communications network (e.g., the Internet) and via one or more software interfaces (e.g., an application program interface (API)), including but not limited to Document Object Model (DOM), Discovery Service (DS), NSUserDefaults, Web Services Description Language (WSDL), Message Exchange Pattern (MEP), Web Distributed Data Exchange (WDDX), Web Hypertext Application Technology Working Group (WHATWG) HTML5 Web Messaging, Representational State Transfer (REST or RESTful web services), Extensible User Interface Protocol (XUP), Simple Object Access Protocol (SOAP), XML Schema Definition (XSD), XML Remote Procedure Call (XML-RPC), or any other mechanisms, open or proprietary, that may achieve similar functionality and results.

Any applicable data structures, file formats, and schemas may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

Such files may follow data models including but not limited to Universal Data Model (UDM), entry-attribute-value (EAV) model, object-attribute-value (OAV) model, vertical database model, open schema, closed schema, or any other standard, nonstandard, or proprietary data models. Configuration data may be structured, unstructured, in flat-file databases, column-oriented databases, row-oriented databases, or other types of database formats.

Any pertinent data, files, and/or databases may be stored, retrieved, accessed, and/or transmitted in human-readable formats such as numeric, textual, graphic, or multimedia formats, further including various types of markup language, among other possible formats. Alternatively or in combination with the above formats, the data, files, and/or databases may be stored, retrieved, accessed, and/or transmitted in binary, encoded, compressed, and/or encrypted formats, or any other machine-readable formats.

The computer system typically includes an operating system and/or other low-level system software configured to support higher-level application software, and interface with system hardware and peripheral devices, managing memory access, input/output (I/O), and process scheduling, for example.

As illustrated in FIG. 6, these peripheral devices may include a storage subsystem 624, comprising a memory subsystem 626 and a file storage subsystem 628, user interface input devices 622, user interface output devices 620, and a network interface subsystem 616. The input and output devices allow user interaction with computer system 610. In the example embodiment illustrated in FIG. 6, the network interface subsystem 616 provides an interface to outside networks, including an interface to a communication network 618, and is coupled via a communication network 618 to corresponding interface devices in other computer systems or machines. The communication network 618 may comprise many interconnected computer systems, machines and communication links. These communication links may be wired links, optical links, wireless links, or any other devices for communication of information. The communication network 618 can be any suitable computer network, for example a wide area network such as the Internet, and/or a local area network such as Ethernet. The communication network 618 can be wired and/or wireless, and the communication network can use encryption and decryption methods, such as is available with a virtual private network. The communication network uses one or more communications interfaces, which can receive data from, and transmit data to, other systems. Embodiments of communications interfaces typically include an Ethernet card, a modem (e.g., telephone, satellite, cable, or ISDN), (asynchronous) digital subscriber line (DSL) unit, IEEE 1394 (Firewire) interface, USB interface, and the like. One or more communications protocols can be used, such as HTTP, TCP/IP, RTP/RTSP, IPX and/or UDP.

The user interface input devices 622 may include an alphanumeric keyboard, a keypad, pointing devices such as a mouse, trackball, touchpad, stylus, or graphics tablet, a scanner, a touchscreen incorporated into the display, audio input devices such as voice recognition systems or microphones, eye-gaze recognition, brainwave pattern recognition, and other types of input devices. Such devices can be connected by wire or wirelessly to a computer system. In general, use of the term "input device" is intended to include all possible types of devices and ways to input information into the computer system 610 or onto the communication network 618. The user interface input devices 622 typically allow a user to select objects, icons, text and the like that appear on some types of user interface output devices, for example, a display subsystem.

The user interface output devices 620 may include a display subsystem, a printer, a fax machine, or non-visual displays such as audio output devices. The display subsystem may include a cathode ray tube (CRT), a flat-panel device such as a liquid crystal display (LCD), a projection device, or some other device for creating a visible image such as a virtual reality system. The display subsystem may also provide non-visual display such as via audio output or tactile output (e.g., vibrations) devices. In general, use of the term "output device" is intended to include all possible types of devices and ways to output information from the computer system 610 to the user or to another machine or computer system.

The memory subsystem 626 typically includes a number of memories including a main random-access memory ("RAM") 630 (or other volatile storage device) for storage of instructions and data during program execution and a read only memory ("ROM") 632 in which fixed instructions are stored. The file storage subsystem 628 provides persistent storage for program and data files, and may include a hard disk drive, a floppy disk drive along with associated removable media, a CD-ROM drive, an optical drive, a flash memory, or removable media cartridges. The databases and modules implementing the functionality of certain embodiments may be stored by file storage subsystem 628.

The bus subsystem 612 provides a device for letting the various components and subsystems of the computer system 610 communicate with each other as intended. Although the bus subsystem 612 is shown schematically as a single bus, alternative embodiments of the bus subsystem may use multiple busses. For example, RAM-based main memory can communicate directly with file storage systems using Direct Memory Access ("DMA") systems.

CONCLUSION

The Detailed Description referred to accompanying figures to illustrate example embodiments consistent with the disclosure. References in the disclosure to "an example embodiment" indicates that the example embodiment described can include a particular feature, structure, or characteristic, but every example embodiment may not necessarily include the particular feature, structure, or characteristic. Moreover, such phrases are not necessarily referring to the same example embodiment. Further, any feature, structure, or characteristic described in connection with an example embodiment can be included, independently or in any combination, with features, structures, or characteristics of other example embodiments whether or not explicitly described.

The Detailed Description is not meant to limiting. Rather, the scope of the disclosure is defined only in accordance with the following claims and their equivalents. It is to be appreciated that the Detailed Description section, and not the Abstract section, is intended to be used to interpret the claims. The Abstract section can set forth one or more, but not all example embodiments, of the disclosure, and thus, are not intended to limit the disclosure and the following claims and their equivalents in any way.

The example embodiments described within the disclosure have been provided for illustrative purposes and are not intended to be limiting. Other example embodiments are possible, and modifications can be made to the example embodiments while remaining within the spirit and scope of the disclosure. The disclosure has been described with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

Embodiments of the disclosure can be implemented in hardware, firmware, software application, or any combination thereof. Embodiments of the disclosure can also be implemented as instructions stored on a machine-readable medium, which can be read and executed by one or more processors. A machine-readable medium can include any mechanism for storing or transmitting information in a form readable by a machine (e.g., a computing circuitry). For example, a machine-readable medium can include non-transitory machine-readable mediums such as read only memory (ROM); random access memory (RAM); magnetic disk storage media; optical storage media; flash memory devices; and others. As another example, the machine-readable medium can include transitory machine-readable medium such as electrical, optical, acoustical, or other forms of propagated signals (e.g., carrier waves, infrared signals, digital signals, etc.). Further, firmware, software application, routines, instructions can be described herein as performing certain actions. However, it should be appreciated that such descriptions are merely for convenience and that such actions in fact result from computing devices, processors, controllers, or other devices executing the firmware, software application, routines, instructions, etc.

The Detailed Description of the example embodiments fully revealed the general nature of the disclosure that others can, by applying knowledge of those skilled in relevant art(s), readily modify and/or adapt for various applications such example embodiments, without undue experimentation, without departing from the spirit and scope of the disclosure. Therefore, such adaptations and modifications are intended to be within the meaning and plurality of equivalents of the example embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

What is claimed is:

1. A magnetic resonance imaging (MRI) system for generating an anatomical image of a patient, the MRI system comprising:

an imaging machine configured to apply magnetic fields and radio frequency waves to a patient within the imaging machine to acquire an image data signal indicative of compositions of tissues within a spatial location of the patient;

a gating signal transmitter configured to compensate for signal offsets and gradient pulse interference that are introduced onto a noisy physiological event signal relating to a physiological event of the patient by the magnetic fields and radio frequency waves, the gating signal transmitter comprising:

a digital gradient offset filter configured to:

evaluate an interference cost function based upon a plurality of characteristics of a first plurality of samples of the noisy physiological event signal that are accumulated during a time interference window to determine a plurality of weights for the first plurality of samples, and identify a second sample from among the first plurality of samples having a least weight from among the plurality of weights during the time interference window to compensate for the signal offsets, and a digital gradient rejection filter configured to perform a non-linear separation technique on a second plurality of samples of the noisy physiological event signal, having the second sample, that are identified over a plurality of time interference windows to provide a plurality of medians values of the second plurality of samples as a third plurality of samples of the noisy physiological event signal to compensate for the gradient pulse interference, and a control system configured to:

trigger the imaging machine to acquire the image data signal based upon the third plurality of samples, and transform the image data signal into the anatomical image to graphically illustrate the compositions of the tissues within the spatial location of the patient.

2. The MRI system of claim 1, wherein the digital gradient offset filter is further configured to identify the second plurality of samples during the plurality of interference time windows, each sample from among the second plurality of samples corresponding to an interference time window from among the plurality of interference time windows.

3. The MRI system of claim 1, wherein the plurality of characteristics of the first plurality of samples comprises volatility of samples from among the first plurality of samples, changes in direction of the samples from among the first plurality of samples, and offsets between the samples from among first plurality of samples.

4. The MRI system of claim 3, wherein the interference cost function is configured to evaluate the volatility of the samples from among the first plurality of samples, the changes in direction of the samples from among the first plurality of samples, and the offsets between the samples from among first plurality of samples to determine the plurality of weights for the first plurality of samples.

5. The MRI system of claim 4, wherein the digital gradient offset filter is configured to identify the second plurality of samples as being samples from among the first plurality of samples having least weights from among the plurality of weights during corresponding time interference windows from among the plurality of time interference windows.

6. The MRI system of claim 1, wherein the digital gradient rejection filter comprises a median filter configured to:

analyze neighboring samples of samples from among the second plurality of samples to determine median values of the neighboring samples; and substitute the median values of the neighboring samples for the samples from among the second plurality of samples to provide the third plurality of samples.

7. A method for operating a magnetic resonance imaging (MRI) system, the method system comprising:

applying, by the MRI system, magnetic fields and radio frequency waves to a patient within an imaging machine to acquire an image data signal indicative of compositions of tissues within a spatial location of the patient;

generating, by the MRI system, a noisy physiological event signal that includes signal offsets and gradient pulse interference introduced onto a physiological event signal relating to a physiological event of the patient by the magnetic fields and radio frequency waves;

evaluating, by the MRI system, an interference cost function based upon a plurality of characteristics of a first plurality of samples of the noisy physiological event signal accumulated during a time interference window to determine a plurality of weights for the first plurality of samples;

identifying, by the MRI system, a second sample from among the first plurality of samples having a least weight from among the plurality of weights during the time interference window to compensate for the signal offsets;

performing, by the MRI system, a non-linear separation technique on a second plurality of samples of the noisy physiological event signal, the second plurality of samples including the second sample and being identified over a plurality of time interference windows;

generating, by the MRI system, a third plurality of samples comprising a plurality of median values of the second plurality of samples to compensate for the gradient pulse interference;

triggering, by the MRI system, the imaging machine to acquire the image data signal based upon the third plurality of samples; and transforming, by the MRI system, the image data signal into an anatomical image that graphically illustrates the compositions of the tissues within the spatial location of the patient.

8. The method of claim 7, further comprising identifying, by the MRI system, the second plurality of samples during the plurality of interference time windows, each sample from among the second plurality of samples corresponding to an interference time window from among the plurality of interference time windows.

9. The method of claim 7, wherein the plurality of characteristics of the first plurality of samples comprises volatility of samples from among the first plurality of samples, changes in direction of the samples from among the first plurality of samples, and offsets between the samples from among first plurality of samples.

10. The method of claim 9, wherein the interference cost function evaluates the volatility of the samples from among the first plurality of samples, the changes in direction of the samples from among the first plurality of samples, and the offsets between the samples from among first plurality of samples to determine the plurality of weights for the first plurality of samples.

11. The method of claim 10, further comprising identifying, by the MRI system, the second plurality of samples as being samples from among the first plurality of samples having least weights from among the plurality of weights during corresponding time interference windows from among the plurality of time interference windows.

12. The method of claim 7, wherein the performing comprises:

analyzing neighboring samples of samples from among the second plurality of samples to determine median values of the neighboring samples; and substituting the median values of the neighboring samples for the samples from among the second plurality of samples.

13. A gating signal transmitter for use with a magnetic resonance imaging (MRI) system to compensate for signal offsets and gradient pulse interference that are introduced onto a noisy physiological event signal relating to a physiological event of a patient, the gating signal transmitter comprising:

a digital gradient offset filter configured to:

evaluate an interference cost function based upon a plurality of characteristics of a first plurality of samples of that noisy physiological event signal that are accumulated during a time interference window to determine a plurality of weights for the first plurality of samples, and identify a second sample from among the first plurality of samples having a least weight from among the plurality of weights during the time interference window to compensate for the signal offsets;

a digital gradient rejection filter configured to perform a non-linear separation technique on a second plurality of samples of the noisy physiological event signal, having the second sample, that are identified over a plurality of time interference windows to provide a plurality of medians values of the second plurality of samples as a third plurality of samples of the noisy physiological event signal to compensate for the gradient pulse interference; and a communications transmitter configured to provide the third plurality of samples to an imaging machine to acquire an image data signal based upon the third plurality of samples.

14. The gating signal transmitter of claim 13, wherein the digital gradient offset filter is further configured to identify the second plurality of samples during the plurality of interference time windows, each sample from among the second plurality of samples corresponding to an interference time window from among the plurality of interference time windows.

15. The gating signal transmitter of claim 13, wherein the plurality of characteristics of the first plurality of samples comprises volatility of samples from among the first plurality of samples, changes in direction of the samples from among the first plurality of samples, and offsets between the samples from among first plurality of samples.

16. The gating signal transmitter of claim 15, wherein the interference cost function is configured to evaluate the volatility of the samples from among the first plurality of samples, the changes in direction of the samples from among the first plurality of samples, and the offsets between the samples from among first plurality of samples to determine the plurality of weights for the first plurality of samples.

17. The MRI gating signal transmitter of claim 16, wherein the digital gradient offset filter is configured to identify the second plurality of samples as being samples from among the first plurality of samples having least weights from among the plurality of weights during corresponding time interference windows from among the plurality of time interference windows.

18. The gating signal transmitter of claim 13, wherein the digital gradient rejection filter comprises a median filter configured to:

analyze neighboring samples of samples from among the second plurality of samples to determine median values of the neighboring samples; and substitute the median values of the neighboring samples for the samples from among the second plurality of samples to provide the third plurality of samples.

* * * * *